US00PP35189P2

(12) United States Plant Patent
Horvath

(10) Patent No.: US PP35,189 P2
(45) Date of Patent: May 23, 2023

(54) ***PENNISETUM ALOPECUROIDES* PLANT NAMED 'WATER TO WINE'**

(50) Latin Name: *Pennisetum alopecuroides*
Varietal Denomination: Water to Wine

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 17/803,150

(22) Filed: Mar. 8, 2022

(51) Int. Cl.
*A01H 5/02* (2018.01)
*A01H 6/46* (2018.01)

(52) U.S. Cl.
USPC ..... Plt./384
CPC ..... *A01H 6/4654* (2018.05)

(58) Field of Classification Search
USPC ..... Plt./384
CPC ..... A01H 6/4654; A01H 5/02
See application file for complete search history.

*Primary Examiner* — Keith O. Robinson

(57) ABSTRACT

A new, distinct *Pennisetum alopecuroides* plant as shown and described, characterized by dark greyed-purple inflorescences on 96 cm stems that start in mid-September in northern Illinois.

1 Drawing Sheet

Figure 1:
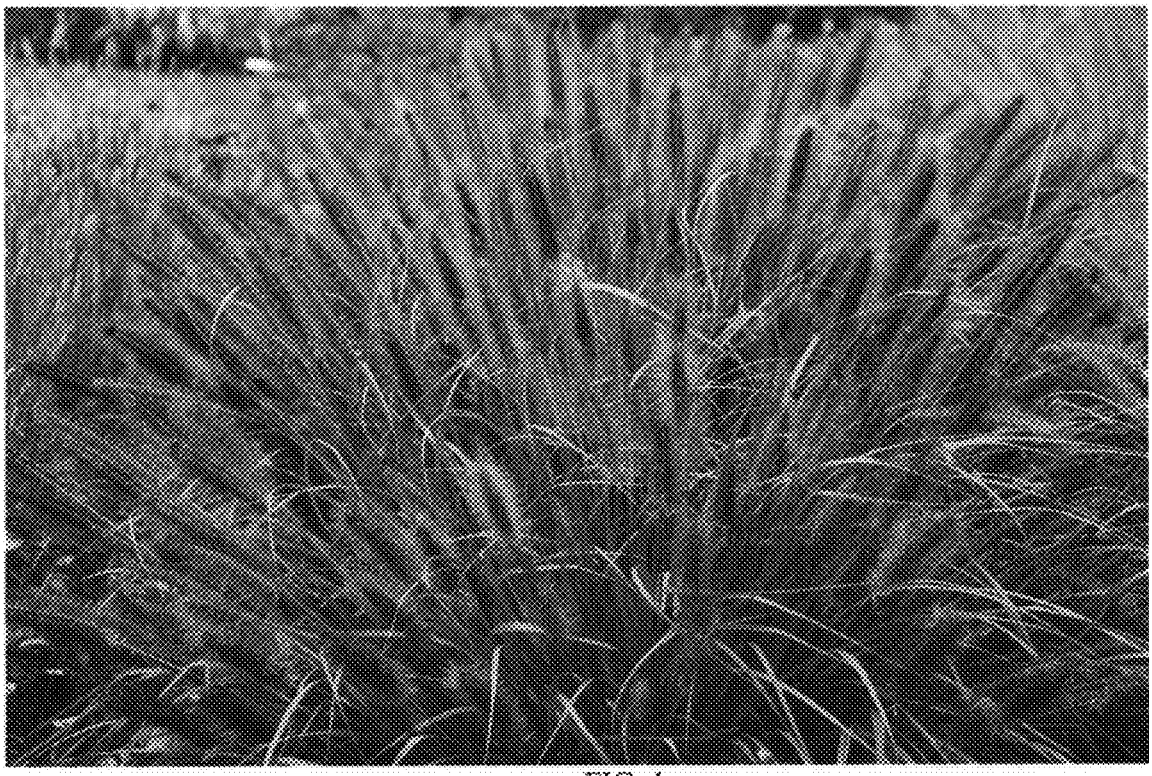

Latin name: *Pennisetum alopecuroides*.
Cultivar name: 'Water to Wine'.

BACKGROUND OF THE INVENTION

The present invention relates to a new form of *Pennisetum alopecuroides* plant named 'Water to Wine'. 'Water to Wine' is a seedling of an unnamed *Pennisetum alopecuroides*, not patented, characterized by dark greyed-purple inflorescences on 96 cm stems that start in late August in northern Illinois. The new plant is the result of a breeding program taking place at a wholesale perennial nursery since 2001. The seedling was grown by the inventor at a wholesale perennial nursery in Hebron, Ill. in 2018. The selection of the new plant was due to its dark greyed-purple inflorescences on 96 cm stems that start in late August in northern Illinois. Asexual, vegetative division propagation has been the only means of reproduction. Propagation has taken place at a wholesale perennial nursery Hebron, Ill. in 2019 to 2021. To date these plants have remained uniform in height. The new *Pennisetum* has shown to be stable and identical in reproduction to the parent after making over 600 vegetative divisions from 2019 to 2021. No plants of the new *Pennisetum alopecuroides* have been sold in this country, or anywhere in the world, prior to the filing of this application, nor has any disclosure of the new plant been made prior to the filing of this application with the exception of that which was disclosed by the inventor within one year of filing of this application and was derived directly from the inventor.

SUMMARY OF THE INVENTION

In the following description, color references are made to The Royal Horticultural Society Colour Chart. The new *Pennisetum alopecuroides* plant named 'Water to Wine' has shown the characteristic of dark greyed-purple inflorescences on 96 cm stems that start in mid-September in northern Illinois.

The parent plants were not available for comparison. Plants of the new *Pennisetum* can be compared to plants of

*Pennisetum alopecuroides* 'Red Head', not patented. 1. The new *Pennisetum* has a height of 96 cm compared to the height of *Pennisetum alopecuroides* 'Red Head' which has a height of 120 cm. 2. The new *Pennisetum* has an inflorescence length of 13 cm compared to *Pennisetum alopecuroides* 'Red Head' which has an inflorescence length of 20 cm.

Plants of the new *Pennisetum* can be compared to plants of *Pennisetum alopecuroides* 'Hameln' not patented. 1. The new *Pennisetum* has a height of 96 cm compared to the height of *Pennisetum alopecuroides* 'Hameln' which has a height of 90 cm. 2. The new *Pennisetum* has an inflorescence length of 13 cm compared to *Pennisetum alopecuroides* 'Hameln' which has an inflorescence length of 10 cm. 3. The new *Pennisetum* has a dark greyed-purple inflorescence color compared to *Pennisetum alopecuroides* 'Hameln' which has a tan inflorescence color.

Plants of the new *Pennisetum* can be compared to plants of *Pennisetum alopecuroides* 'Mondry', not patented. 1. The new *Pennisetum* has a height of 96 cm compared to the height of *Pennisetum alopecuroides* 'Mondry' which has a height closer to 60 cm. 2. The new *Pennisetum* has a mid-September bloom time compared to *Pennisetum alopecuroides* 'Mondry' which typically blooms in October.

DESCRIPTION OF PHOTOGRAPHS

FIG. 1. Shows a mature 2 year old plant in Glencoe, Ill. USA.

Figure 2:
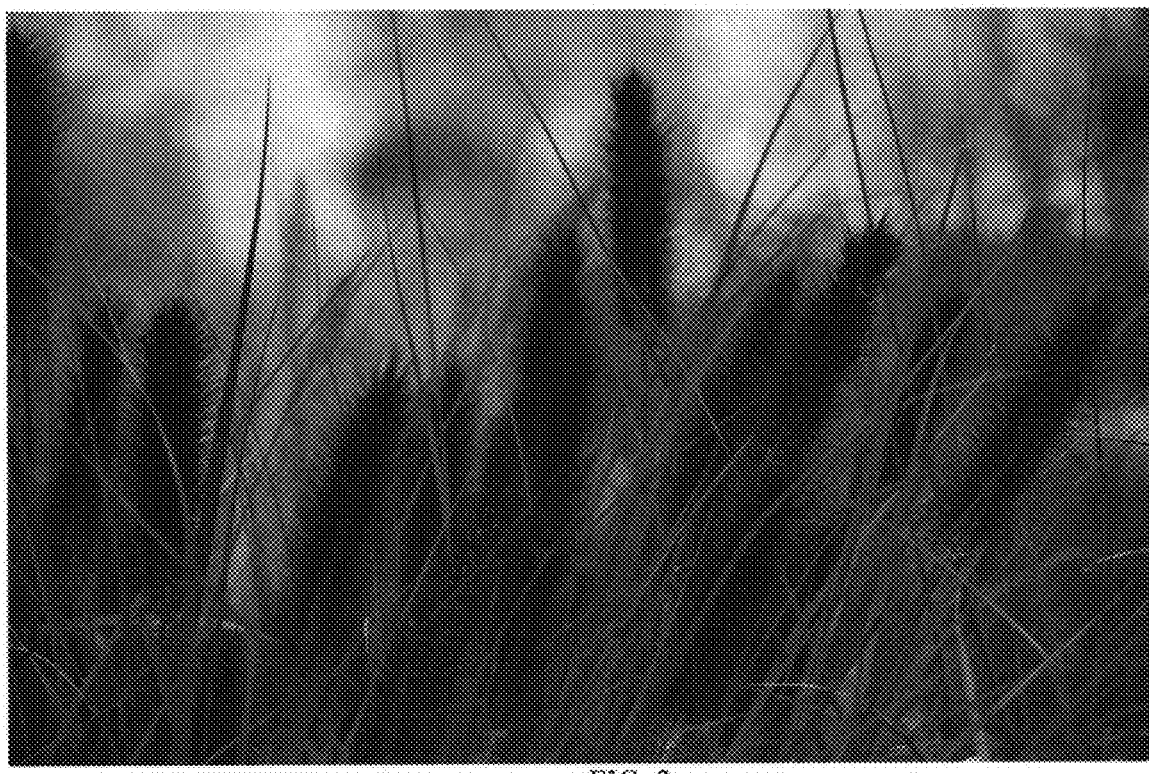

FIG. 2. Shows a close up of the flowers in Hebron, Ill. USA.

DETAILED BOTANICAL DESCRIPTION

In the following description, color references are made to The Royal Horticultural Society Colour Chart (2001). The plant herein described is a two year old, three gallon specimen grown in full sun and irrigated in Hebron, Ill.

Botanical classification: *Pennisetum alopecuroides* cultivar 'Water to Wine'.

Parentage: An open pollinated cross of two different *Pennisetum alopecuroides* that were unnamed selections.

Propagation: Vegetative division.

Plant description: Overall habit of the new *Pennisetum* is strongly clumping mounds with upright stems topped by dark greyed-purple colored inflorescences in early September. Vigor is moderate to fast.

*Plant height.*—96 cm.

*Plant width.*—75 cm.

*Stem diameter.*—8 mm.

*Stem color.*—147 A.

Foliage:

*Type.*—Deciduous, grass growing in culms.

*Shape.*—Linear.

*Petiole.*—None.

*Blade length.*—33 cm average, ranging from 18-55 cm.

*Width.*—9 mm.

*Adaxial leaf description.*—The leaf color is green color close 137 A.

*Abaxial leaf description.*—The leaf color is green color 147 A.

*Basal leaf sheath color.*—Close to 147 A.

*Leaf sheath.*—Glabrous.

*Auricles.*—Not present.

*Ligules.*—As wide as the leaf blade, up to 1 mm tall, color close to 147 A.

*Collars.*—Continuous, as wide as the leaf blade, less than 1 mm tall, color close to 147 A.

*Leafbuds are folded in the bud stage.*

*Rhizomes or stolons.*—None.

*The attitude of the tiller on the culm is erect,* 20 *degrees from the culm.*

*The culm node is glabrous and color at the node is close to* 147 *A.*

*Internode.*—Length 20-25 cm. 6-7 cm at the base, 22 cm above that.

*Culm diameter and color at the internode.*—7 mm, close to 147 A.

*Fall leaf color.*—Mostly green 137 A with some 187 C fall color at the tips.

Flower inflorescence:

*Number of spike bearing tillers in the culmus.*—60.

*Inflorescence type.*—Terminal bristled spike.

*Floret color.*—*N*186 A.

*Individual floret size.*—2 mm across, 9 mm tall.

*Anther coloration and size.*—183 B, 6 mm long, 1 mm wide.

*Stigma color and size.*—Close to 155 B, 13 mm long, 1 mm wide.

*Glume color and size.*—Close to 186 A, 3 mm, less than 1 mm wide.

*Bristle size.*—24 mm long, less than 1 mm wide.

*Bristle color.*—186 A. Bristle number — 20-30.

*Caryopsis color.*—144 A, shape — elliptic.

*Panicles.*—A dense terminal, spike. 7 cm wide, and 13 cm long.

*Overall inflorescence spike size.*—7 cm wide, 13 cm long.

*Flower number.*—Approximately 130 florets per mature spike measuring 7 cm wide, 13 cm long.

*Fertility.*—Self-fertile, Fertile with 3 Anthers and 3 Stamens, 1 Stigma.

*Blooming habit.*—Terminal bristled spike on up to 96 cm stems.

*Bloom period and duration.*—Mid-September into October.

*Scent.*—No scent noticed.

*Bloom color emerging.*—*N*77 A, overall — N186 A.

*Roots.*—Stiff, fibrous, and freely branching.

*Fruit.*—Seed identical to the species except color is N186 A.

Disease resistance: Plants are not susceptible to any major pests or diseases.

I claim:

1. A new, distinct *Pennisetum alopecuroides* plant named 'Water to Wine' as shown and described, characterized by dark greyed-purple inflorescences on 96 cm stems that start in mid-September in northern Illinois.

* * * * *